(12) United States Patent
Schadt et al.

(10) Patent No.: US 6,205,869 B1
(45) Date of Patent: Mar. 27, 2001

(54) APPARATUS AND METHOD FOR SAMPLING FLUID FROM REACTOR VESSEL

(75) Inventors: John C. Schadt, Watertown; Eugene R. Rommelfaenger, Neosho; Michael D. Farrell, Brookfield, all of WI (US)

(73) Assignee: Sentry Equipment Corporation, Oconomowoc, WI (US)

( * ) Notice: Subject to any disclaimer, the term of this patent is extended or adjusted under 35 U.S.C. 154(b) by 0 days.

(21) Appl. No.: 09/373,450

(22) Filed: Aug. 12, 1999

(51) Int. Cl.[7] ................................................. G01N 1/20
(52) U.S. Cl. ............................................... 73/863.71
(58) Field of Search ........................... 73/863.71, 863.72, 73/863.81, 863.83, 863.85, 863.86, 864.34

(56) References Cited

U.S. PATENT DOCUMENTS

| | | | |
|---|---|---|---|
| 3,798,962 | * | 3/1974 | Collins, Jr. ..................... 73/863.71 |
| 4,628,749 | * | 12/1986 | Rafter, Jr. ..................... 73/863.71 |
| 5,029,485 | * | 7/1991 | Marr . | |
| 5,296,197 | * | 3/1994 | Newberg et al. ................ 73/863.81 |
| 5,408,889 | * | 4/1995 | Parault ............................ 73/864.34 |

FOREIGN PATENT DOCUMENTS

1360346 * 7/1974 (GB) ................... 73/863.83

OTHER PUBLICATIONS

Marketing Product Update—Grinnell Corporation—PV Reactor Sampling Systems for Continuous Media Circulation and PH Monitoring Technova—Safesamp—Reactor Sampling Systems RSS Series; No Date.

* cited by examiner

Primary Examiner—Robert Raevis
(74) Attorney, Agent, or Firm—Jansson, Shupe, Munger & Stomma Ltd.

(57) ABSTRACT

A fluid-sampling method and apparatus are disclosed. The apparatus includes a valve assembly, an overflow chamber assembly, a vacuum assembly and a sample bottle mounting assembly in particular arrangements. In certain preferred embodiments the overflow chamber assembly has an inner vessel, preferably a standpipe, within an outer vessel which forms an overflow chamber in which fluid from the standpipe can be viewed. The valve assembly preferably includes a sampling valve with an outer shell, an insert member and a pivotable valve member therein. The pivotable valve member preferably has a main body portion with first and second circumferential grooves therein and a diagonal bore therethrough for properly directing fluid from and through particular ports in the insert member based on the position of the valve member. The method includes drawing the fluid from the reactor vessel through a valve assembly into an inner vessel of an overflow chamber assembly, overflowing the fluid from the inner vessel into an outer vessel of the overflow chamber assembly, and thereafter retrieving a sample from the inner vessel.

20 Claims, 7 Drawing Sheets

APPARATUS AND METHOD FOR SAMPLING FLUID FROM REACTOR VESSEL

FIELD OF THE INVENTION

The present invention generally relates to the sampling of fluid for testing and, more particularly, to apparatus and methods for periodically sampling fluids from reactor vessels while reactions are in progress.

BACKGROUND OF THE INVENTION

A variety of systems for sampling fluids from reactors and tanks are known. However, numerous disadvantages and shortcomings exist with prior systems, and there is a need for improvement to overcome such disadvantages and shortcomings.

Some examples of commercially-available prior fluid-sampling devices are the "Safesamp Reactor Sampling Systems" sold by Technova AG, of Sweden, and the "Neotecha Sampling Systems" sold by Grinnell Corporation, of Exeter, N.H.

The Safesamp system's basic arrangement includes a flanged dip pipe for connection to the tank with the dip pipe extending downwardly into the fluid in the tank, a bottom flange with a suction hose mounted at the top and extending downward through the dip pipe and into the tank fluid and a perpendicular connection port in communication with the dip pipe to pressurize the tank. The bottom flange is connected to a flanged "charging" ball valve. A middle flange is connected to the charging valve and has a sightglass with a ball float mounted on top and a perpendicular port located below the sightglass to direct flow for sampling. An upper flange is mounted on top of the sightglass and includes the sightglass ball seat, perpendicular connections for auxiliaries and a perpendicular port for a vent return. The perpendicular sampling port located in the middle flange is connected to a flanged isolation ball valve which is connected to the sampling assembly. The sampling assembly includes a sample bottle which is vented through another isolation ball valve which is connected to the vent return port in the upper flange.

To obtain a sample, the "charging" ball valve is opened (the sampling isolation valve is closed) and the fluid is drawn up through the suction tube (by supplying, if need, a vacuum via the upper flange connection or pressurizing the tank via the lower flange connection). The fluid flows upwardly, fills the perpendicular sampling port in the middle flange (to the isolation ball valve) and continues filling the sightglass. As fluid fills the sightglass, the ball float rises with the level until it reaches the top of the sightglass where the ball then seats against the ball seat located in the upper flange and flow stops. The operator closes the "charging" ball valve and opens the sampling isolation valve and the vent valve. The fluid flows by gravity from the sightglass through the perpendicular sampling port in the middle flange, through the sampling isolation valve and into the sample bottle. Any entrapped gases are vented through the vent connection located between the sampling bottle and the vent return line.

The above-described sampling system has drawbacks in that the sample fluid volume would consist of partial previous sampling fluid if the system is not purged after each sampling, or would nonetheless consist of the first volume of fluid that is drawn from the top of the tank without any system fluid flushing first. It would be preferable to drain off the first and perhaps subsequent volumes of fluid so that the fluid sent to the sampling bottle is a sample that has not been mixed with previous samples or other contaminants. Such sampling system can only get an unmixed sample within the sampling bottle by drawing numerous cycles of fluid through the system. This is a time-consuming and inconvenient process, and is wasteful of the often expensive chemicals being mixed in the reactor vessel.

The aforementioned Neotecha systems, sold by Grinnell Corporation, are generally similar to the above-described Safesamp Samplers. The Neotecha system samples fluid from reactors for continuous media circulation and pH monitoring. The Neotecha samplers utilize double-diaphragm pumps and are relatively compact in design. The Neotecha samplers also use lined stainless steel braided hoses and connections to facilitate quick start-ups and convenient changes. They have a pH probe connection device which allows adaptation to most commercially-available pH probes, and various auxiliary ports to facilitate cleaning of wetted surfaces and additional vessel access.

However, the Neotecha systems have the problem that, when chemical compositions in the reactor vessel have particulates or become viscous to some extent, the compositions can tend to clog or damage the pump. This leads to costly down time for cleaning and repair.

These and other existing devices for sampling fluids from reactor vessels have significant problems. This invention addresses and overcomes such problems.

OBJECTS OF THE INVENTION

An object of the present invention is to provide an improved fluid-sampling apparatus which easily and reliably gives properly-representative samples from a reactor vessel.

Another object of this invention is to provide an improved in-process fluid-sampling apparatus which is reliably useful for a wide variety of reaction fluids, including mixtures with significant particulates and/or raised viscosities.

Yet another object of this invention is to provide an improved fluid-sampling apparatus which gives reliably-representative samples quickly, without any need for repeated withdrawal of fluids from the reactor vessel.

Another object of the invention is to provide an improved fluid-sampling apparatus which avoids waste of valuable reaction fluids.

Another object of the invention is to provide an improved fluid-sampling apparatus which avoids or minimizes significant downtime for cleaning and repair and which is easy to flush for cleaning and easy to disassemble for repair.

Still another object of the invention is to provide an apparatus for sampling fluid from a reactor vessel without contaminating the vacuum source used to draw the sample, while at the same time not requiring flushing of the sample or multiple cycling of the sample through a sight glass.

Another object of the invention is to provide improved fluid-sampling methods which overcome certain problems of existing methods and apparatus.

SUMMARY OF THE INVENTION

The present invention relates to an improved fluid-sampling method and apparatus for sampling fluid from a reactor vessel.

The fluid-sampling apparatus of this invention includes a valve assembly, an overflow chamber assembly connected to the valve assembly, a vacuum assembly connected to the overflow chamber assembly, and a sample bottle mounting assembly connected to both the valve assembly and the vacuum assembly. The overflow assembly allows easy drawing of reaction fluid from the reactor into the sampling apparatus and thereafter allows a controlled overflow of withdrawn fluid inside the sampling apparatus, all done in a manner such that a sample may easily be taken from a portion of the withdrawn fluid isolated from the potentially-problematic first-out fluid, and such that all unused non-sample fluid returns to the reactor vessel without any external exposure or loss. The structure of the fluid-sampling apparatus of this invention makes this possible.

In preferred embodiments, the valve assembly includes a sampling valve with an insert member within an outer shell and a valve member pivotable within the insert member to direct reactor fluids—first to, and then in two ways from, the aforesaid overflow chamber assembly. The overflow chamber assembly includes an inner vessel from which reactor fluids can (1) first overflow into an outer sealed vessel also containing the inner vessel and (2) subsequently be withdrawn as non-first-out samples. The valve assembly facilitates such withdrawing of samples and the return of overflowed and unused liquids to the reactor vessel.

In preferred forms, the fluid-sampling apparatus includes a legend plate inscribed with instructive words (such as "FILL," "SAMPLE" and "DRAIN") corresponding to three predetermined positions of the pivotable valve member, and a handle connected to the pivotable valve member with an indicator (preferably a pointer) thereon movable with respect to the legend plate to indicate the desired fluid movements.

The pivotable valve member preferably has a main body portion with first and second circumferential grooves therein and a diagonal bore therethrough and a second portion for connection to a handle for pivoting the pivotable valve member. The insert member housing the pivotable valve member preferably has first, second, third and fourth ports leading from various positions on an outer periphery thereof to the central location or space therein in which the pivotable valve member is situated, such that when the pivotable valve member is pivoted to first, second and third predetermined positions, the first and second circumferential grooves in and the diagonal bore of the pivot member are appropriately aligned with the first, second, third and fourth ports in the insert member to achieve the desired fluid movement.

In certain preferred forms, the outer shell in which the insert member is held has an open top and the insert member has an upwardly-extending portion extending through the open top, such upwardly-extending portion having a tapered top drain surface converging downwardly to the first port to facilitate drainage, the top drain surface also having the second port laterally offset from the first port.

The insert member also preferably has a tubular lower portion extending through the outer shell, such tubular lower portion having the third port, which accommodates fluid flow from and back to the reactor.

In highly preferred embodiments, alluded to above, the overflow chamber assembly includes an inner vessel in the form of a standpipe communicating through an open lower end with the second port and having an open top end, and at least a portion of the outer vessel is transparent for viewing inside the overflow chamber. The outer vessel is preferably a transparent tube. The preferred standpipe inside the outer vessel most preferably has a tapered inside bottom surface for preventing a fluid from remaining within the standpipe. In highly preferred embodiments, the outer vessel of the overflow chamber assembly has a volume capacity of at least fifteen times the volume capacity of the inner vessel, thereby to assure capacity for fluid overflowing from the standpipe.

Preferred embodiments have a ball check valve as assurance against contamination of the vacuum assembly.

In preferred embodiments, when the pivotable valve member is in a first predetermined position, the aforementioned diagonal bore therein is aligned to form part of the fluid inflow passageway, thereby allowing flow of fluid from the reactor vessel, in sequence, through the third port in the insert member, through the diagonal bore in the pivotable valve member, through the offset second port in the insert member, and through the inner vessel (preferably the aforementioned standpipe) to overflow therefrom into the outer vessel. When the pivotable valve member is in a second predetermined position, the aforementioned second circumferential groove is aligned to form the middle portion of the first fluid flow outflow passageway, thereby allowing flow of fluid from the inner vessel to the sample bottle—by flow in sequence back through the second port in the insert member, through the second circumferential groove in the pivotable valve member, through the laterally-located fourth port in the insert member, and through the sample bottle mounting assembly. And, when the pivotable valve member is in the third predetermined position, the aforementioned first circumferential groove is aligned to form the middle portion of the second outflow passageway, thereby allowing fluid flow from the outer vessel to the reactor vessel—by flow in sequence through the first port (the drain port) in the insert member, through the first circumferential groove in the pivotable valve member, and back through the third port in the insert member and so on.

In highly preferred embodiments, the first circumferential groove spans approximately 180 degrees about the pivotable valve member, and the second circumferential groove spans approximately 90 degrees about the pivotable valve member.

The sample bottle mounting assembly includes a sample bottle connected to a sample bottle adapter. The sample bottle adapter is friction fit within a sample bottle mounting block which is connected in cantilever fashion to a side of the valve assembly using a mounting support plate. The sample bottle mounting block has a tubular portion extending from a side thereof The tubular extending member is friction fit to the insert member in fluid-flow relation to the fourth port in the insert member. The sample bottle is secured at its top outer periphery to an inner periphery of the sample bottle adapter. The sample bottle mounting assembly includes a dip tube through which fluid from the overflow chamber assembly enters the sample bottle. The sample bottle preferably has a volumetric capacity greater than the volumetric capacity of the standpipe (or other inner vessel) of the overflow chamber assembly to prevent overfilling of the sample bottle. The sample bottle is preferably vented to the overflow chamber of the overflow chamber assembly so no vapors are released from a sample of fluid transferred to the sample bottle.

The method of this invention includes attaching a fluid-sampling apparatus to the reactor vessel, vacuum drawing fluid from the reactor vessel through a valve assembly of the fluid-sampling apparatus and into an inner vessel in an overflow chamber assembly, overflowing the fluid from the inner vessel into an outer vessel of the overflow chamber assembly, and discontinuing the vacuum drawing.

In preferred forms, the method also includes the step, carried out after discontinuing the vacuum drawing, of pivoting a pivotable valve member to a sample position so that fluid in the inner vessel drains by gravity into a sample bottle. It is most preferred, after fluid drains to the sample bottle, to pivot the pivotable valve member to a drain position so that fluid which has overflowed into the outer vessel drains by gravity into the reactor vessel.

BRIEF DESCRIPTION OF THE DRAWING FIGURES

DETAILED DESCRIPTIONS OF PREFERRED EMBODIMENTS

Figure 1:
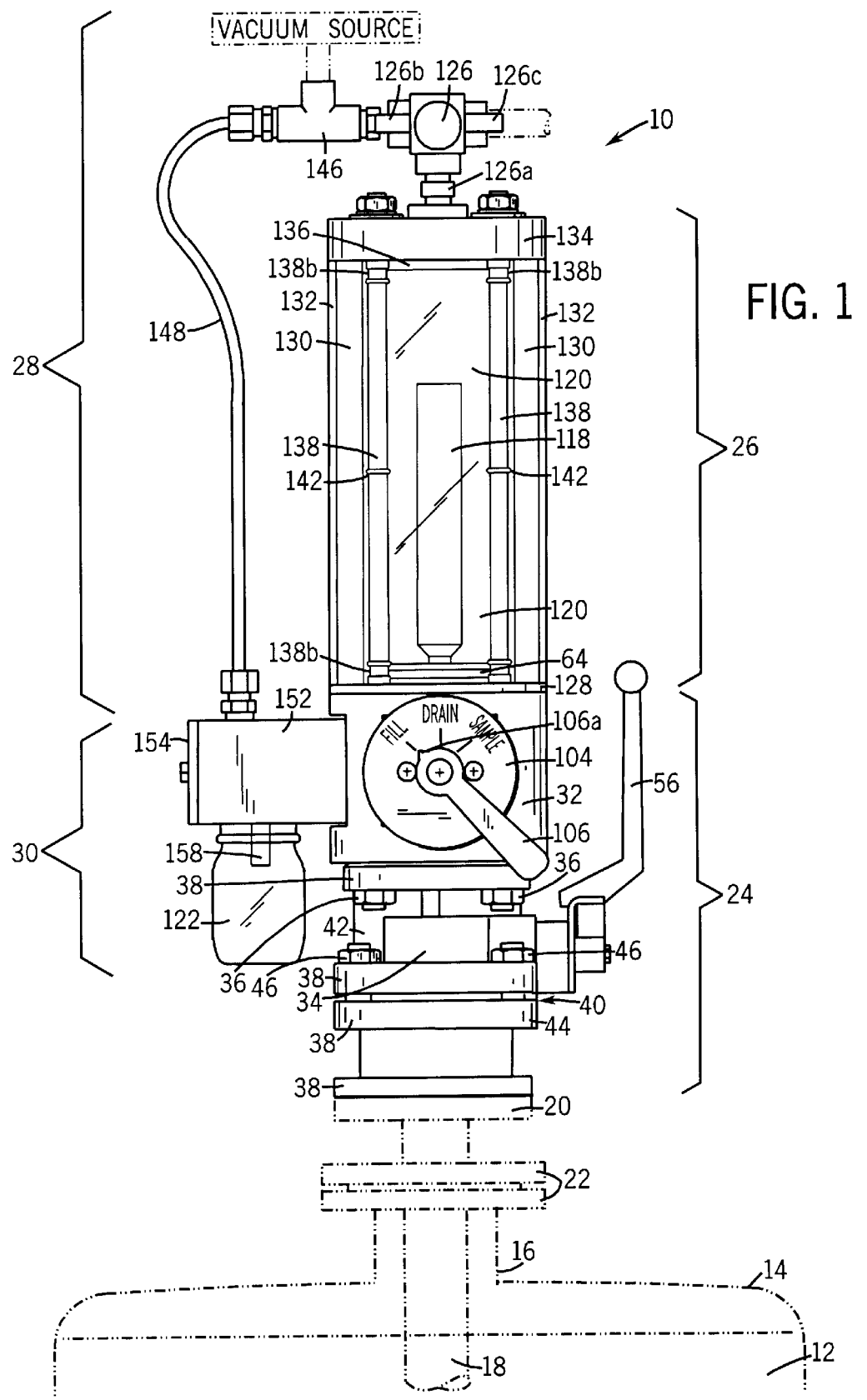
FIG. 1 is a front elevation of a fluid-sampling apparatus of the present invention.
Figure 2:
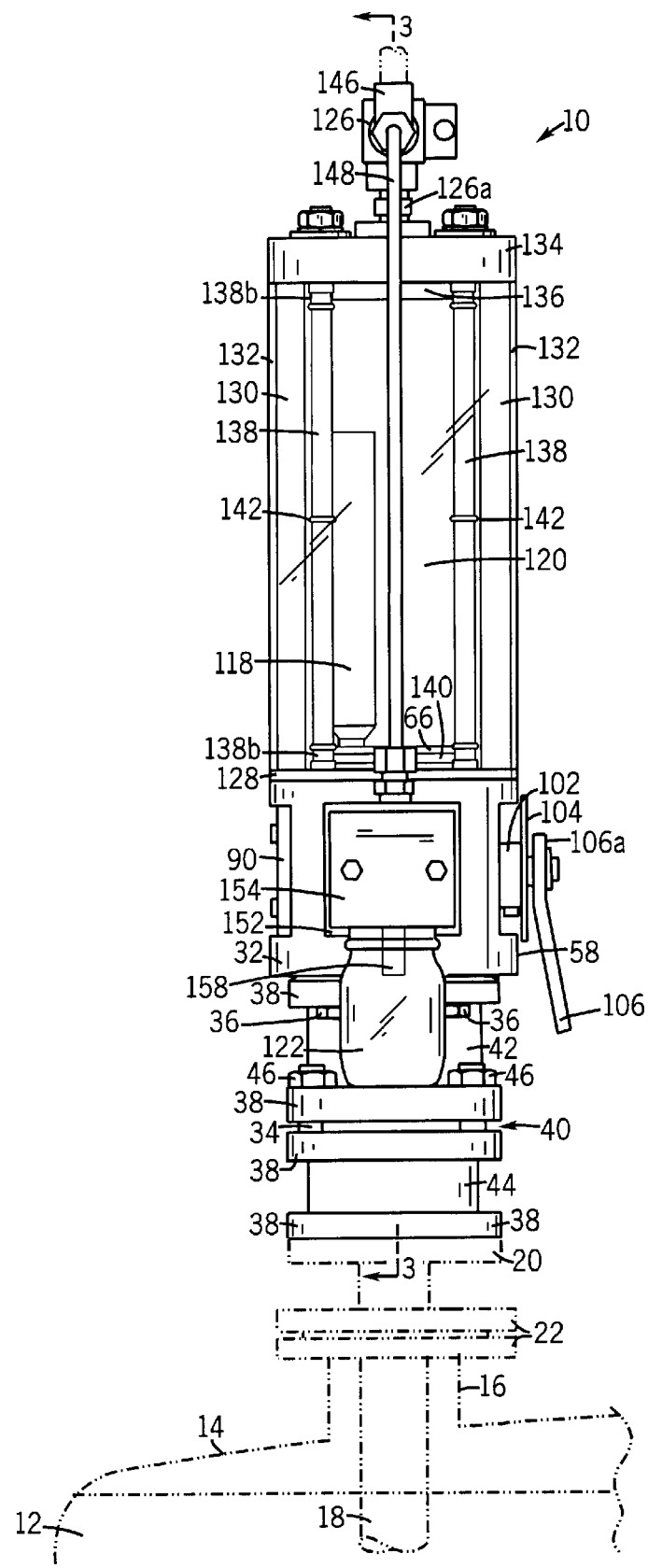
FIG. 2 is a left side elevation of the fluid-sampling apparatus of FIG. 1.

FIGS. 1 and 2 illustrate a fluid-sampling apparatus 10 for sampling fluid 12 from a reactor vessel 14. Fluid-sampling apparatus 10 is mounted on top of a sampling port 16 of reactor vessel 14. A dip tube 18, having either a single flange 20 or a double flange 22 (as denoted in dashed outline) at the top thereof, is connected to the bottom of fluid-sampling apparatus 10. Dip tube 18 extends through sampling port 16 of reactor vessel 14 into fluid 12 at the top of reactor vessel 14.

Fluid-sampling apparatus 10 includes: a valve assembly 24; a overflow chamber assembly 26; a vacuum assembly 28; and a sample bottle mounting assembly 30. Each of valve assembly 24, overflow chamber assembly 26, vacuum assembly 28, and sample bottle mounting assembly 30 is comprised of various component parts which will be explained below.

Valve assembly 24 includes a sampling valve 32 mounted on top of a ball valve 34. The bottom of sampling valve 32 is connected to the top of ball valve 34 via mating fasteners or the like in known fashion, as illustrated in several of the drawing figures.

Details of ball valve 34 will not be described, since they are well known in the art. An acceptable ball valve 34 is a Richter™ Fluoroplastic Lined Valve for Corrosive Applications (KNA Full Port Series), manufactured by ITT Engineered Valves. It is noted, however, than handle 56 of ball valve 34 controls the operation thereof, and that ball valve 34 serves typical shut-off and flow functions.

Referring now to the cross-sectional views of FIGS. 3 and 9–13, sampling valve 32, which is connected to the top of ball valve 34, will now be explained in more detail. It should be noted that the combination of sampling valve 32 and ball valve 34 provides for double block isolation from reactor vessel 14. Sampling valve 32 includes an outer shell 58 for housing an insert member 60 therewithin. Outer shell 58 has an open top for sliding insertion of insert member 60 thereinto. Outer shell 58 has front, back, left-hand side, right-hand side, and bottom surfaces. Each of the front, back, left-hand side, and bottom surfaces of shell 58 has apertures therethrough. Each of the front, back, and lenthand side surfaces of outer shell 58 of sampling valve 32 are somewhat "indented" or "two-tiered" as shown in FIGS. 1 and 2 so that flanges formed at the top and bottom of the front, back, and left-hand sides of sampling valve 32 protrude more horizontally outwardly than do the actual surface of the front, back, and left hand sides of sampling valve 32. This indented wall surface arrangement is for positioning of a member between the flanges as will be explained in more detail below.

Insert member 60 is a somewhat squarish block of material, preferably made of a virgin Teflon material, with various extensions therefrom and spaces, ports, etc. therein. More particularly, insert member 60 has an upwardly-extending top portion 64 which extends through the open top of outer shell 58 and a tubular lower portion 66. Insert member 60 has a space therein for receiving a pivotable valve member (hereafter described). Such space within insert member 60 leads from a smaller diameter opening in the front surface of insert member 60 to a larger diameter opening in the back surface of insert member 60. There are also first, second, third and fourth ports 74, 76, 78 and 80 leading from the space within insert member 60 to various positions on the outer periphery of insert member 60. Second and fourth ports 76 and 80 have widened-diameter opening portions located immediately adjacent the outer periphery of insert member 60, as can be best seen in FIGS. 3 and 9. These facilitate the connection of other fluid-flow devices, as now explained.

One widened-diameter opening portion is on top of insert member 60 and allows insertion of a key portion of overflow chamber assembly 26. Such portion of overflow chamber assembly 26 is inserted into and secured to such widened-diameter opening portion of the insert member 60 in fluid-flow relationship to second port 76.

The other widened-diameter opening portion is laterally located on insert member 60, and allows insertion and securement of sample bottle mounting assembly 30, in fluid-flow relationship to fourth port 80.

When insert member 60 is within shell 58, its tubular lower portion 66 extends through the bottom surface of shell 58 of sampling valve 32. Tubular lower portion also provides a fluid-flow path from reactor vessel 14, including third port 78 in insert member 60.

Figure 7:
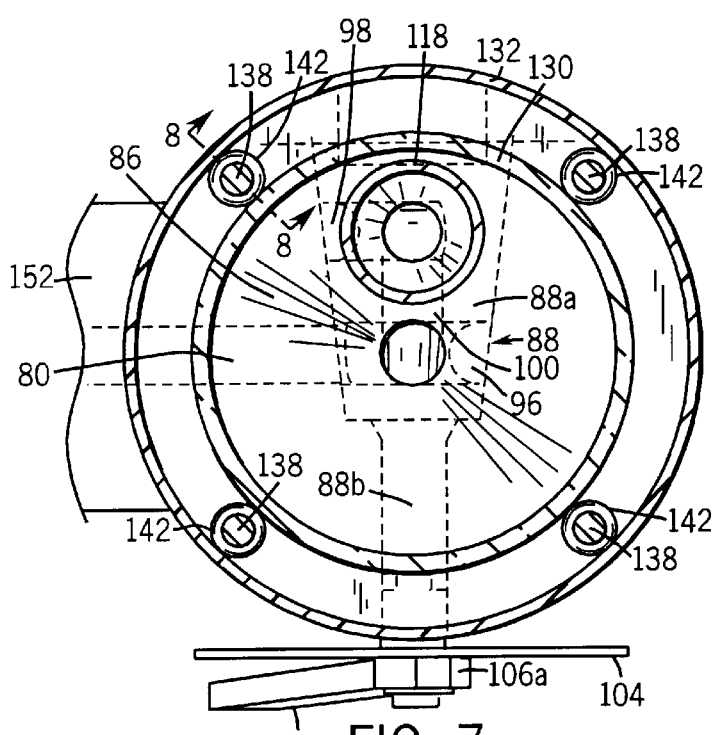
FIG. 7 is a cross-sectional view through the fluid-sampling apparatus, taken along section 7—7 as indicated in FIG. 3.
Figure 8:
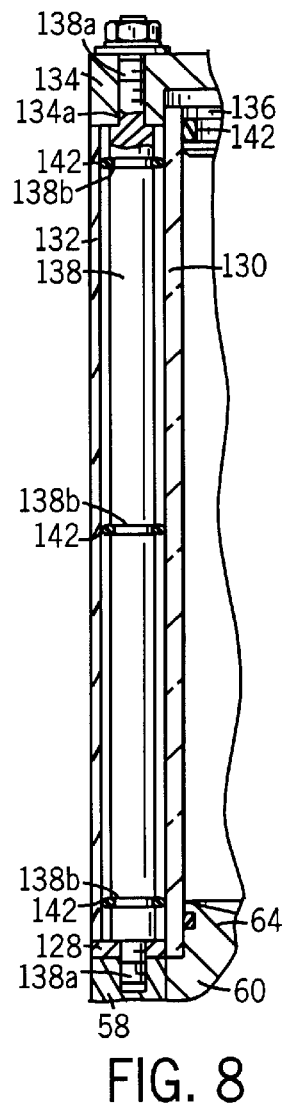
FIG. 8 is a partial cross-sectional view of a tie rod of the fluid-sampling apparatus, taken along section line 8—8 as indicated in FIG. 7.

Upwardly-extending top portion 64 of insert member 60 has a tapered top drain surface 86 which is downwardly tapered toward its middle, as seen in FIG. 7. The angle of taper of tapered top drain surface 86 is preferably about fifteen degrees to facilitate drainage of fluid 12 by gravity from overflow chamber assembly 26.

Figures 3, 9:
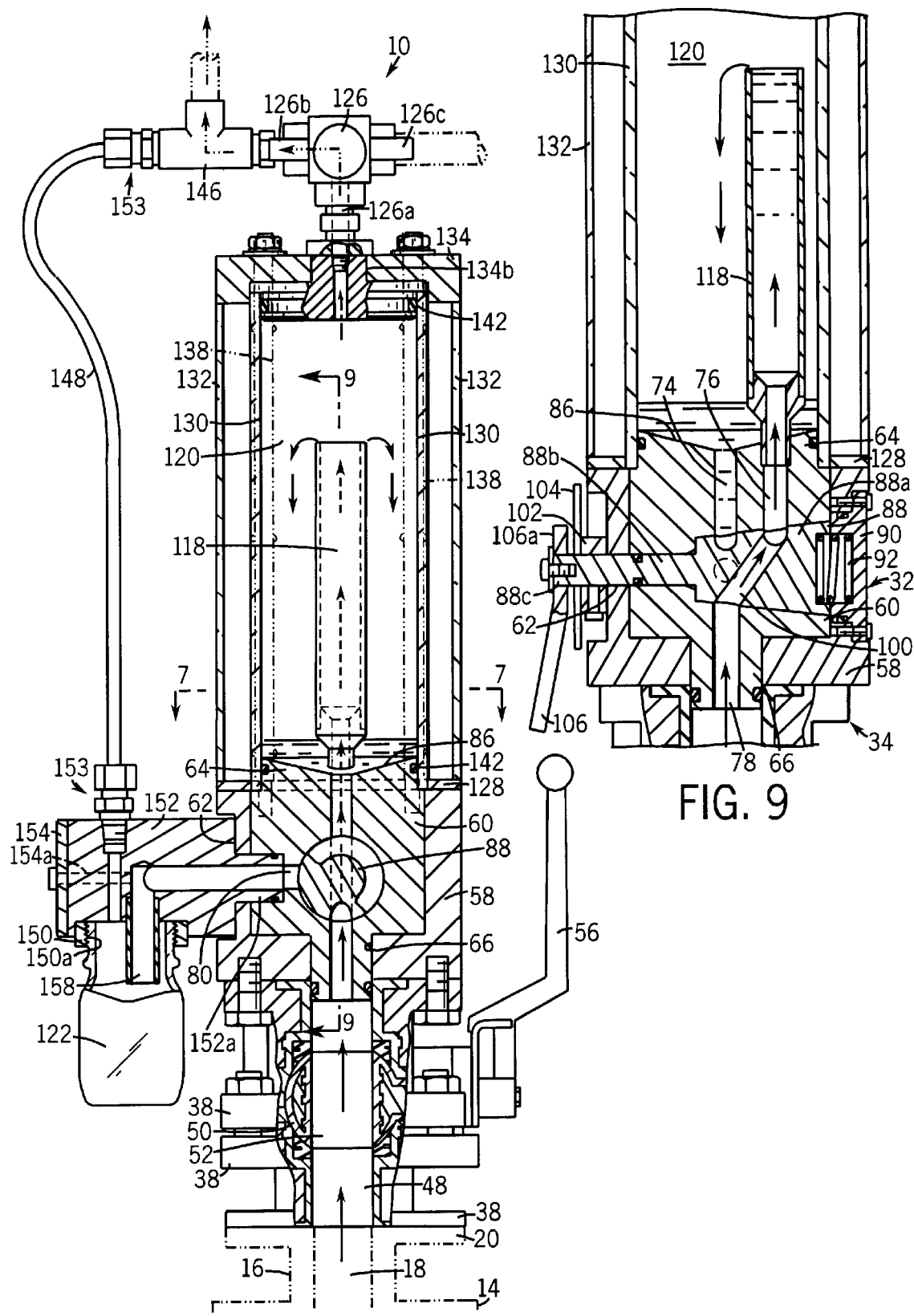
FIG. 3 is a cross-sectional view taken along section 3—3 as indicated in FIG. 2.
FIG. 9 is a partial cross-sectional view through the fluid-sampling apparatus, taken along section 9—9 as indicated in FIG. 3, showing the fluid-sampling apparatus in fill mode wherein fluid can be vacuum drawn from the reactor vessel, through the valve assembly, into the standpipe so as to overflow into the overflow chamber.
Figure 13:
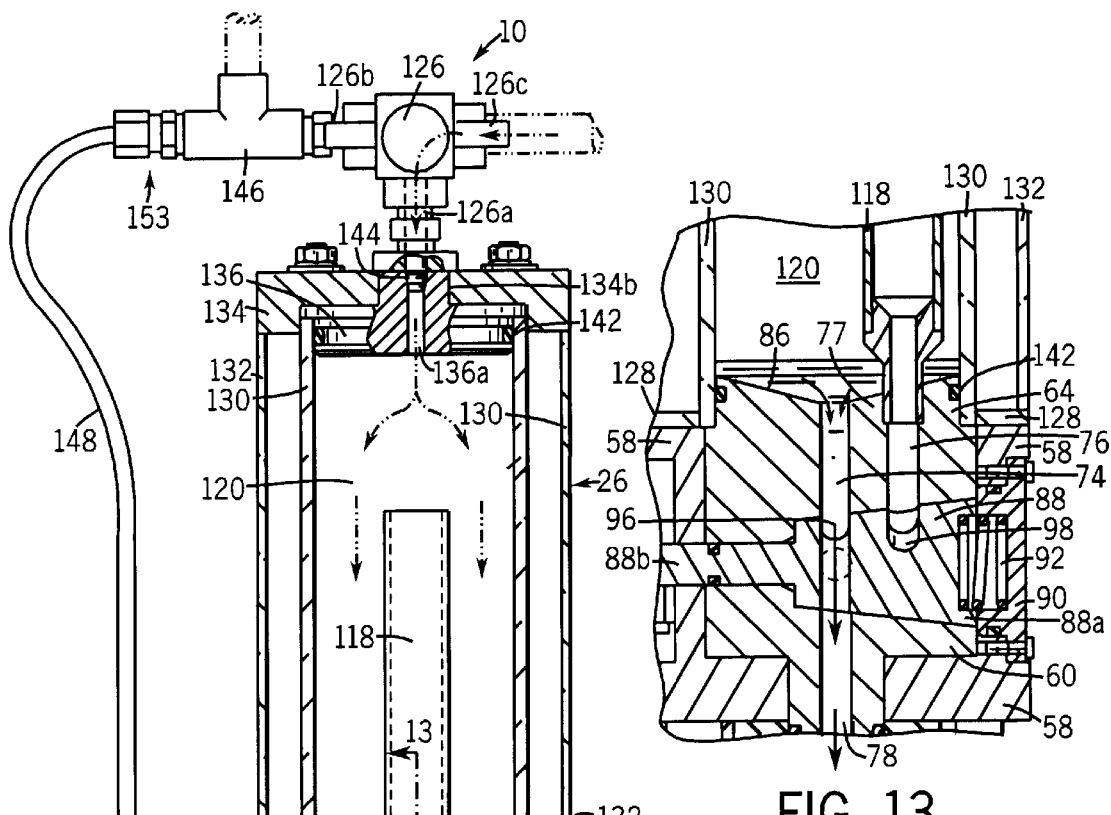
FIG. 13 is a partial cross-sectional view through the fluid-handling apparatus of the present invention, taken along section 13—13 as indicated in FIG. 12.

Referring to FIGS. 9 and 13, the void space within insert member 60 is for housing a pivotable valve member 88. Such void space is joined to the first, second, third and fourth ports 74, 76, 78 and 80 for fluid flow from such space to the periphery of insert member 60. That is, first, second, third and fourth ports 74, 76, 78 and 80 lead from such space to various locations on the outer periphery. First, second, third and fourth ports 74, 76, 78 and 80 are aligned with apertures in the surfaces of shell 58 of sampling valve 28.

Pivotable valve member 88 is slidingly received into the space in insert member 60 such that it is tightly housed therewithin while still able to pivot within insert member 60. This is accomplished by subjecting pivotable valve member 88 to an extremely cold temperature prior to its insertion within the void space within insert member 60. The cold temperature causes pivotable valve member 88, which is preferably made of a Hastelloy® B-2 material, to contract somewhat. While pivotable valve member 88 is still in its contracted state, it is slidingly inserted into the void space within insert member 60. Once pivotable valve member 88 has been inserted into insert member 60, it is allowed to warm up to room temperature so that pivotable valve member 88 expands to fit tightly and precisely within the space within insert member 60. However, despite its tight fit, pivotable valve member 88 is still capable of pivoting within insert member 60.

Figures 10, 11:
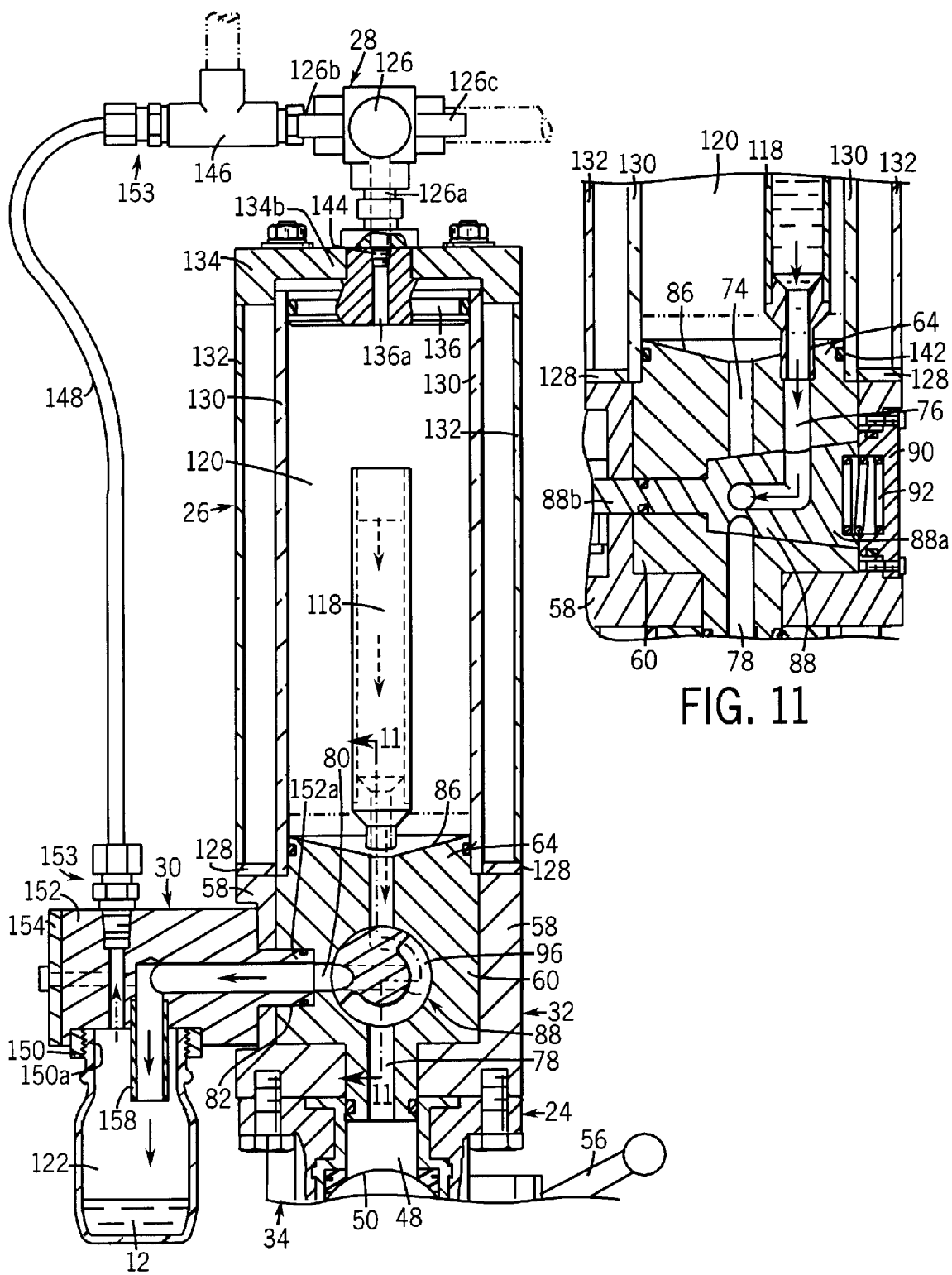
FIG. 10 is a partial cross-sectional view through the fluid-sampling apparatus showing the same cross-section as FIG. 3, except that the pivotable valve member of the fluid-sampling apparatus has been pivoted so that the apparatus is in sampling mode wherein the fluid left in the standpipe can be drained by gravity into the sample bottle.
FIG. 11 is a partial cross-sectional view through the fluid-sampling apparatus, taken along section 11—11 of FIG. 10, showing how the pivotable valve member is spring-loaded within the fluid-sampling apparatus.

Pivotable valve member 88 is preferably spring-loaded within insert member 60 by means of a spring retainer member 90 and spring 92. Referring to FIGS. 9, 11, and 13, the somewhat stepped or two-tiered configuration of spring retainer member 90 is such that spring 92 can be inserted between an indentation in spring retainer member 90 and an indentation in the larger diameter end of main body portion 88a of pivotable valve member 88 in order for pivotable valve member 88 to be spring loaded within insert member 60.

Referring to FIGS. 3 and 9–13, ports 74, 76, 78 and 80 through insert member 60 are illustrated. More particularly, first, second and third ports are best seen in FIGS. 9, 11, and 13, and the fourth port is best viewed in FIGS. 3, 10, and 12. Ports 74, 76, 78 and 80 lead from an outer peripheral surface of insert member 60 to the space within insert member 60 for housing pivotable valve member 88. Ports 74, 76, 78 and 80 are preferably of a slightly oversized diameter, for instance, approximately nine millimeters. This relatively large diameter and the fact that ports 74, 76, 78 and 80 are relatively short ensures that there is little possibility for them to become plugged up while fluid-sampling apparatus 10 is in operation, even if the fluid being sampled is of high viscosity or has particulate matter therein.

First port 74 is located through the approximate center of tapered top drain surface 86 of upwardly-extending top portion 64 of insert member 60 above the space in insert member 60 occupied by pivotable valve member 88. In other words, first port 74 leads from tapered top drain surface 86 to the space where pivotable valve member 88 is housed within insert member 60.

Second port 76 is parallel to but horizontally offset from first port 74. As already noted, second port 76 leads from a point on tapered top surface 86 to the space within insert member 60 where pivotable valve member 88 is housed. Second port 76 includes a recess 77 of a larger diameter extending downwardly from a point on tapered top surface 86.

Third port 78 extends through the center of tubular lower portion 66 of insert member 60, through the lower portion of insert member 60 to the space within insert member 60 where, as already noted, pivotable valve member 88 is housed within insert member 60.

Finally, fourth port 80 extends through the side of insert member 60 and leads to the space in insert member 60 where pivotable valve member 88 is located.

First, second, third and fourth ports 74, 76, 78, and 80 are open or closed to the passage of fluid 12 therethrough depending upon the orientation of pivotable valve member 88 within insert member 60, as will be explained in more detail below.

Figure 4:
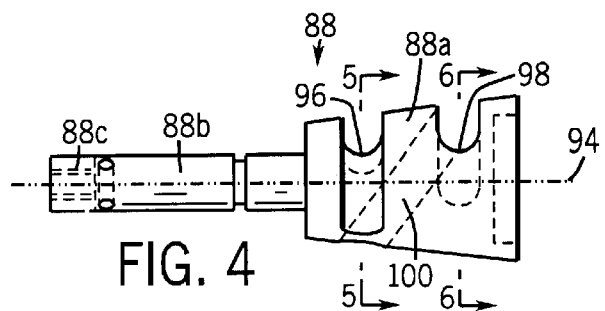
FIG. 4 is a side elevation of a pivotable valve member of the fluid-sampling apparatus.

Referring to FIG. 4, pivotable valve member 88 is made up of first, second and third integral parts 88a, 88b and 88c. The first part or main body portion 88a of pivotable valve member 88 is cylindrical in shape and tapers from a first larger diameter end to a second smaller diameter end.

The second part or valve stem portion 88b of pivotable valve member 88 is uniformly cylindrical in shape along its length and is smaller in diameter than the diameter of the second smaller diameter end of main body portion 88a of pivotable valve member 88. Valve stem portion 88b extends between the small diameter end of main body portion 88a and the third part or pivot handle portion 88c. Pivot handle portion 88c is of a typical tab configuration having two parallel sides joined on each end by a radius to receive a like-shaped connection portion of a pivot handle. That is, pivot handle portion 88c is of a hockey rink configuration. The diameter between the two radius ends is the same diameter of valve stem portion 88b. Pivot handle portion 88c includes a threaded bore along the central longitudinal axis 94 of valve member 88 used to secure a pivot handle thereto.

Figures 5, 6:
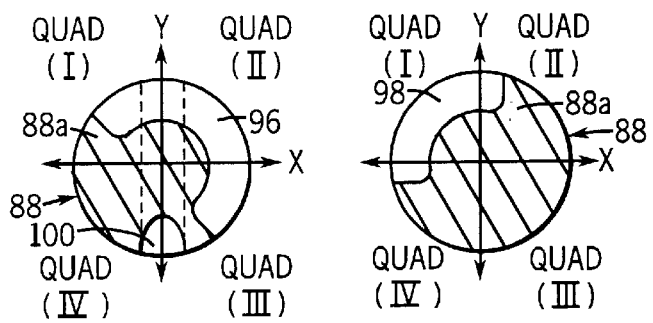
FIG. 5 is a cross-sectional view through the pivotable valve member, taken along section 5—5 as indicated in FIG. 4.
FIG. 6 is cross-sectional view through the pivotable valve member, taken along section 6—6 as indicated in FIG. 4.

Pivotable valve member 88 has first and second circumferential grooves 96, 98 in an outer periphery of main body portion 88a thereof First circumferential groove 96 is nearer the second smaller diameter end of main body portion 88a of pivotable valve member 88. As shown in FIG. 5, first circumferential groove 96 extends for approximately one-hundred-eighty degrees (i.e., from a starting point approximately at a forty-five degree middle of a first quadrant (I), through an entire ninety degrees of a second quadrant (II), and to an ending point at approximately a forty-five degree middle of a third quadrant (III)) around the outer periphery of main body portion 88a of pivotable valve member 88.

Second circumferential groove 98 is nearer the first larger diameter end of main body portion 88a of pivotable valve member 88. As shown in FIG. 6, second circumferential groove 98 extends approximately ninety degrees (i.e., from an approximate zero degrees of the first quadrant (I) to an approximate ninety degrees of the first quadrant(I)) around the outer periphery of main body portion 88a of pivotable valve member 88.

Pivotable valve member 88 has a diagonal bore 100 through main body portion 88a thereof Diagonal bore 100 extends from the approximate end point of second circumferential groove 98 (see FIG. 4) in the outer periphery of main body portion 88a of pivotable valve member 88 (i.e., from an approximate ninety degrees of the first quadrant (I)) to a point (i.e., approximately ninety degrees of the third quadrant (III); see FIG. 5) which is close to the ending point of first circumferential groove 96 in the outer periphery of main body portion 88a of pivotable valve member 88 (i.e., an approximate forty-five degrees of the third quadrant (III)).

Referring to FIG. 9, valve stem portion 88b and pivot handle portion 88c of pivotable valve member 88 extend through front surface of shell 58 of sampling valve 32, through a detent plate 102 and a legend plate 104. A pivot handle 106 is attached to pivot handle portion 88c of pivotable valve member 88 by a washer and fastener combination. Detent plate 102 fits in the indentation in the front surface of shell 58 of sampling valve 32 and is of a generally rectangular shape. Detent plate 102 has a central cradle of a size to accommodate valve stem portion 88b. The central cradle includes a centrally located half-moon bore portion whose parallel side walls first extend upwardly then extend at an outward angle to a point at the top of detent plate 102. Detent plate 102 includes a threaded bore located centrally on the underside of detent plate 102 extending upwardly and terminating at the bore cradle portion. Detent plate 102 also includes two mounting bores located on either side of the central cradle. Legend plate 104 is a flat, annular member having a central bore through which valve stem portion 88b extends and has an outer diameter larger than the indentation in the front surface of shell 58. Legend plate 104 includes inscriptions for three positions thereon, a first position entitled "FILL" which corresponds to a fill mode of fluid-sampling apparatus 10, a second position entitled "DRAIN" which corresponds to a drain mode of fluid-sampling apparatus 10, and a third position entitled "SAMPLE" which corresponds to a sample mode of fluid-sampling apparatus 10. Legend plate 104 includes two mounting bores located on either side of the central bore, such mounting bores align with mounting bores of detent plate 102. Legend plate 104 and detent plate 102 are attached to the front surface shell 58 of sampling valve 32 via fasteners, such as bolts, through the aligned mounting bores and into apertures in the front surface of shell 58.

Pivot handle 106 may be pivoted through an angle of about 90 degrees. When pointer 106a of pivot handle 106 is pivoted so as to point toward the word "FILL" inscribed on legend plate 104 as in FIGS. 1 and 14, pivotable valve member 88 is pivoted so that diagonal bore 100 through pivotable valve member 88 is aligned to connect second port 76 within insert member 60 to third port 78 within insert member 60 as shown in FIG. 9, so that fluid 12 can be drawn, by vacuum or otherwise, from reactor vessel 14 to a first vessel or standpipe 118 to overflow into a second vessel or overflow chamber 120 of overflow chamber assembly 26, as explained in more detail below.

When pointer 106a of pivot handle 106 is pivoted so as to point toward the word "SAMPLE" inscribed on legend plate 104, pivotable valve member 88 is pivoted so that second circumferential groove 98 in the outer periphery of pivotable valve member 88 is aligned to connect second port 76 to fourth port 80 as shown in FIG. 10, so that fluid 12 can drain by gravity from standpipe 118 of overflow chamber assembly 26 to a sample bottle 122 of sample bottle mounting assembly 30. In the alternative, fluid 12 can be pushed via purge connection of three-way valve 126 of vacuum assembly 30 from standpipe 118 of overflow chamber assembly 26 to sample bottle 122.

When pointer 106a of pivot handle 106 is pivoted so as to point toward the word "DRAIN" inscribed on legend plate 104, pivotable valve member 88 is pivoted so that first circumferential groove 96 in the outer periphery of pivotable valve member 88 is aligned to connect first port 74 to third port 78 as shown in FIG. 13, so that fluid 12 can drain by gravity (or if necessary can be pushed via purge connection of three-way valve 126 of vacuum assembly 30 from overflow chamber 120 of overflow chamber assembly 26) to reactor vessel 14.

Referring to FIGS. 1, 2, 3, and 9–14, overflow chamber assembly 26 will now be described in more detail. Overflow chamber assembly 26 includes: a retainer ring 128 for fitting around upwardly-extending top portion 64 of sampling valve 32; a first vessel or standpipe 118 is friction fitted within recess 77 (of second port 76) located at an offset position in tapered top drain surface 86; a second vessel or overflow chamber 120 which is formed by a transparent, borosilicate glass tube 130 (as its sidewall), and retainer ring 128 and tapered top surface 86 of upwardly-extending top portion 64 (as its bottom surface); a transparent, outer protective plastic tubular covering 132 surrounding glass tube 130; an upper ring member 134 with an upper insert member 136 fitted at least partially therewithin for acting as a cover or top for overflow chamber 120; and a plurality of tie rods 138 for tying upper ring member 134 to the top of sampling valve 32.

Retainer ring 128 sits atop shell 58 of sampling valve 32. Upwardly-extending top portion 64 of insert member 60 extends vertically upwardly past the top of retainer ring 128, as shown in FIGS. 1 and 2. Upwardly-extending top portion 64 has a circumferential groove 140 in its sidewall to accept an O-ring 142 which acts as a seal against the inner periphery of glass tube 130.

Tie rods 138, preferably made of stainless steel, are used to connect valve assembly 24 to upper ring member 134 of overflow chamber assembly 26. The plurality of tie rods 138 are adjacent to the outer periphery of glass tube 130. Each tie rod 138 has first and second threaded ends 138a. First ends 138a mate with threaded apertures 144 in the top of insert member 60. Second threaded ends 138a extend through non-threaded apertures in upper ring member 134; nuts are secured to second threaded ends 138a to fasten upper ring member 134 and upper insert member 136 as a cover over overflow chamber assembly 26.

Tie rods 138 have spaced circumferential grooves 138b along a length thereof Grooves 138b are for acceptance of O-ring members 142 to serve as protective spacers between tie rods 138 and the outer periphery of precision-ground glass tube 130 and the inner periphery of outer plastic protective covering 132.

Transparent tube 132, made of plastic, preferably acrylic, is placed around glass tube 130 to act as a protective cover.

Standpipe 118 is an inner first vessel housed within outer second vessel or overflow chamber 120, which is formed by glass tube 130 and the other nearby structure. Standpipe 118 has an open top with a large opening and an open bottom with a smaller opening. Standpipe 118 has a tapered inside bottom surface which allows standpipe 118 to drain easily and completely by gravity. Standpipe 118 has a transparent tube portion and funnel-like bottom portion. The bottom portion of standpipe 118 terminates in an outlet tube of a narrower diameter which is friction fit into recess 77 of second port 76 in insert member 60. Standpipe 118 stands upright on insert member 60.

An upper ring member 134 has a plurality of holes 134a therethrough, preferably four evenly spaced approximately ninety degrees apart, for acceptance of threaded ends 138a at the top of tie rods 138 therethrough. Holes 134a are preferably situated so as to be at a distance approximately equal to the thickness of plastic tubular covering 132 from the outer periphery of upper ring member 134. There is a stepped aperture 134b at the center of upper ring member 134. In other words, near the top surface of upper ring member 134, there is an aperture of a first, smaller diameter. The aperture of the first, smaller diameter only goes through about half the thickness (i.e., the top half) of upper ring member 134 and leads to an aperture of a second, larger diameter which is adjacent the lower surface of upper ring member 134, and which also only goes through about half (i.e., the lower half) of the thickness of upper ring member 134. This stepped aperture 134b is used to partially house upper insert member 136.

Upper insert member 136 is a somewhat stepped, annular member having a lower portion of a diameter approximately equal to or slightly smaller than the second, larger diameter of stepped aperture 134b of upper ring member 134 so that at least an upper portion of the lower portion of upper insert member 136 fits within the second, larger diameter of stepped aperture 134b of upper ring member 134. Upper insert member 136 also has an upper portion of a diameter approximately equal to or slightly smaller than the first, smaller diameter of stepped aperture 134b of upper ring member 134 in order that at least a lower portion of the upper portion of upper insert member 136 fits within the first, smaller diameter of stepped aperture 134b of upper ring member 134.

Figure 12:
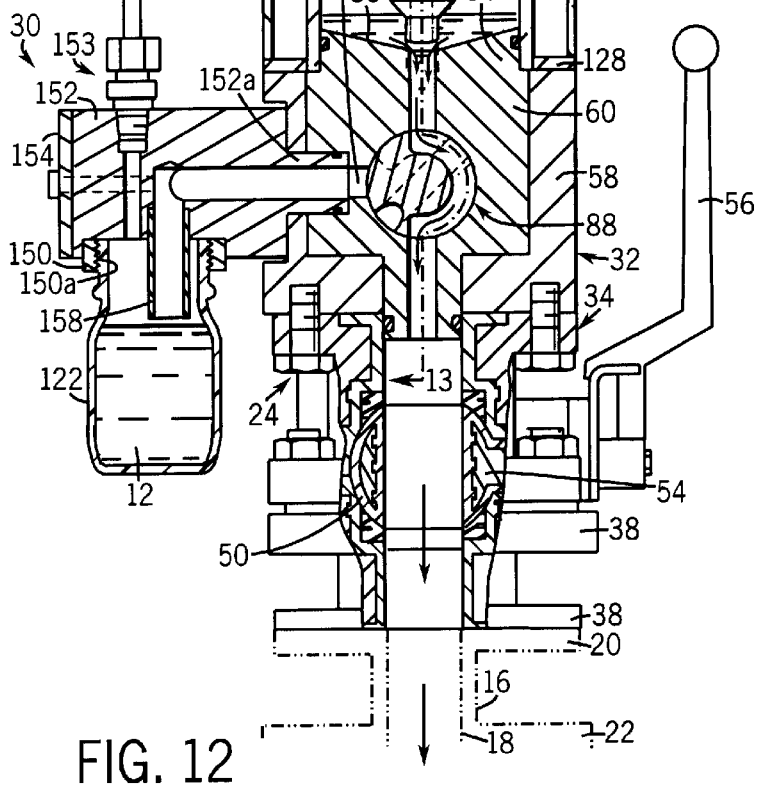
FIG. 12 is a partial cross-sectional view showing the same cross-section as in FIGS. 3 and 10, except that the pivotable valve member has been pivoted so that the apparatus is in the drain mode, allowing fluid in the overflow chamber to either be drained by gravity or purged back to the reactor vessel.

As best seen on FIGS. 10 and 12, upper insert member 136 has a cylindrical aperture 136a at a center thereof The upper portion of cylindrical aperture 136a includes a tapered, threaded portion for mating with a threaded tube 144 leading from a first port or vacuum/purge inlet 126a of three-way valve 126 of vacuum assembly 28.

The preferred embodiment of fluid-sampling apparatus 10 of the present invention has a vacuum assembly 28. Fluid-sampling apparatus 10 may also be used on reactor tanks or vessels that operate at a positive pressure of 90 psi (i.e., 6 bar), in which case, vacuum assembly 28 would not be needed, but some external valving modifications would be required.

When a vacuum assembly 28 is used, the vacuum assembly would include a three-way valve 126 having: a first port or vacuum/purge inlet 126a threadingly connected to upper insert member 136 of overflow chamber assembly 26; a second port 126b connected to a vacuum connection 146, which is in turn connected to a vacuum source; and a third port 126c being connectable, if necessary, to a flush/purge connection and a flush/purge source. Vacuum assembly 28 would also include Teflon hose or other tubing 148 leading from vacuum connection 146 to sample bottle mounting assembly 30.

Sample bottle mounting assembly 30 includes: sample bottle 122; a sample bottle adapter 150; sample bottle mounting block 152; and a sample bottle mount support plate 154.

Sample bottle mounting block 152 has a laterally-extending tubular male portion 152a received within a lateral female receptacle in insert member 60, so that sample mounting block 152 is in fluid-flow engagement with fourth port 80 in insert member 60. In this way, sample bottle mounting block 152 is mounted to the side of sampling valve 32 in a cantilever fashion. Such mounting is between upper and lower flanges on the outside periphery of shell 58.

The inner diameter of tubular male portion 152a coincides with a port leading to sample bottle dip tube 158. Sample bottle dip tube 158 passes through sample bottle adapter 150 and into sample bottle 122.

Sample bottle mounting block 152 also includes a port through the height of mounting block 152 leading from the top surface thereof to a top surface of an aperture within the bottom of mounting block 152. The aperture is for friction-fit acceptance of sample bottle adapter 150. A port through the height of mounting block 152 has a top portion which is tapered and threaded for mating acceptance of a compression fitting 153 for connection of tubing 148 leading from vacuum connection 146. It should be noted that sample bottle 122 is vented in such a way that any vapors released from the sample of fluid 12 in sample bottle 122 are returned to overflow chamber 120 of overflow chamber assembly 26.

Sample bottle adapter 150 is an annular member having a female threaded aperture 150a at the center thereof for threadingly mating with a male threaded open end of sample bottle 122. Sample bottle adapter 150 is held suspendedly from sample bottle mounting block 152 by a friction fit mount or equivalent.

Sample bottle mount support plate 154 is generally square and has at least two holes 154a through a thickness thereof, holes 154a being for acceptance of fasteners, most preferably bolts, for securing mounting block 152 to the side of sampling valve 32.

Fluid-sampling apparatus 10 of the present invention which is made of the above-described parts is easily flushed for cleaning out the internal workings thereof Furthermore, fluid-sampling apparatus 10 is easy to disassemble for replacement of worn or damaged parts. Pivotable valve member 88 of fluid-sampling apparatus 10 is designed so that if cross-flow leakage occurs within sampling valve 32 due to valve misalignment, there is no consequence on the representivity of sample of fluid 12. This is because the head or height of the fluid in standpipe 118 is always higher than the head or height of fluid 12 in overflow chamber 120. Thus, even if there is cross-flow leakage, it is always from a contemporaneous sample of fluid 12 to an old sample of fluid 12 so that contamination is prevented.

Figure 14:
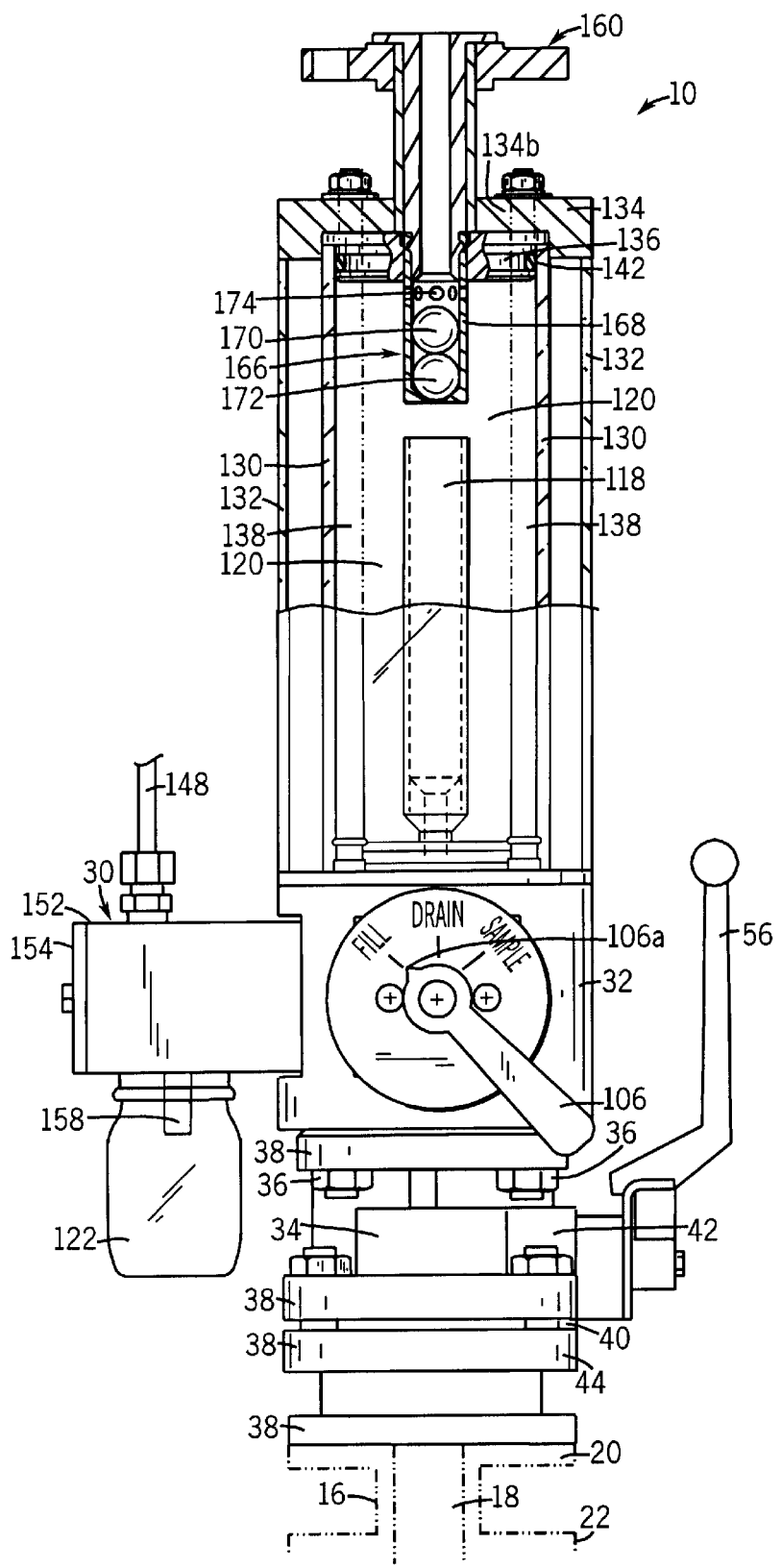
FIG. 14 is another embodiment of the apparatus of the present invention, incorporating a ball check valve to ensure that fluid does not get into the vacuum connection.

Referring to FIG. 14, a second embodiment of fluid-sampling apparatus 10 of the present invention is illustrated. In the second embodiment, a ball check valve 166 is suspended from upper insert member 136 at least partially housed within upper ring member 134. Ball check valve 166 has a central tubular member 168 which contains a first upper floatable ball 170 and a second, lower floatable ball 172 therein. The central tubular member 168 has small apertures 174 evenly spaced around the outer periphery thereof at a height from the bottom of central tubular member 168 approximately equal to twice the diameter of one of balls 170, 172. In this way, upper floatable ball 170 never touches fluid 12 being vacuum-drawn from reactor vessel 14, because as lower floatable ball 172 rises with the fluid level, it pushes upper floatable ball 170 upwardly until upper floatable ball 170 passes small apertures 174 and cuts off the vacuum, sealing the overflow chamber 120 and preventing fluid 12 from getting into and contaminating the first port or vacuum/purge inlet 126a of three way valve 126.

In operation, fluid-sampling apparatus 10 of the present invention is designed to sample fluid 12 from a reactor vessel 14. Reactor vessel 14 may be used, for example, for pharmaceutical applications in which a large vessel is needed for mixing and reacting compositions for manufacture of various drugs.

Fluid-sampling apparatus 10 of the present invention generally works as follows:

Initially, ball valve 34 of valve assembly 24 is closed and sampling valve 32 is in drain mode, where it was at the end of the last fill-sample-drain cycle. Handle 106 of sampling valve 32 is in a position so that pointer 106a on handle 106 of sampling valve 32 points toward the word "DRAIN" on legend plate 104 and pivotable valve member 88 is in the drain position wherein the first or central upper port 74 of sampling valve 32 is connected to the third or central lower port 78 of sampling valve 32 via first circumferential groove 96 in the outer periphery of pivotable valve member 88.

To begin a new cycle, handle 56 of ball valve 34 is pivoted so that ball valve 34 is opened. Then, handle 106 of sampling valve 32 is pivoted until pointer 106a of handle 106 of sampling valve 32 points towards the word "FILL." When three-way valve 126 is opened to vacuum connection 146 so that when the vacuum source is turned on, fluid 12 is drawn upwardly from reactor vessel 14 through dip tube 18 situated in sampling port 16, through ball valve 34, through the third or central lower port 78 in sampling valve 32, through diagonal bore 100 in pivotable valve member 88 of sampling valve 32, through the second or upper, horizontally-offset port 76 in sampling valve 32 and into standpipe 118.

As fluid 12 continues to be drawn upwardly, it eventually fills standpipe 118, begins to overflow from standpipe 118, and collects in overflow chamber 120. The pressure differential between standpipe 118 and overflow chamber 120 ensures that fluid 12 drawn from reactor vessel 14 does not flow into vacuum assembly 28, but instead drops to the bottom of overflow chamber 120. The pressure differential between standpipe 118 and overflow chamber 120 is due in part to the relative difference in their volumetric capacities. More particularly, standpipe 118 is capable of holding a liquid volume capacity of approximately sixty milliliters, whereas overflow chamber 120 is capable of holding a liquid volume capacity of approximately one liter. In the second embodiment, ball check valve 166 also helps to ensure that fluid 12 being drawn from reactor vessel 14 is not drawn into vacuum assembly 28.

When fluid 12 in overflow chamber 120 is about two-thirds the height of standpipe 118, which can be observed through the transparent walls of the overflow chamber, vacuum connection 146 is closed and ball valve 34 is closed so that no more fluid 12 can be drawn from reactor vessel 14. Fluid 12 in standpipe 118 is the end flow product—an accurately representative sample from the reactor vessel, because all of the "dead sample" has overflowed into overflow chamber 120.

Since standpipe 118 has a volume of approximately sixty milliliters and overflow chamber 120 has an approximate volume of one liter, the volume of fluid 12 needed to be overflowed from dip tube 18 to overflow chamber 120 can be calculated by determining the volume of sample in dip tube 18. This volume is multiplied by two or three to arrive at the overflow volume required. Then the height can be marked on outer plastic covering 132 of overflow chamber assembly 26 and the vacuum source can be shut off when fluid 12 in overflow chamber 120 reaches this height. Through experimentation, applicants have learned that overflow volume of half the height of dip tube 18 is sufficient to receive a properly representative sample of fluid 12 in standpipe 118.

Handle 106 of sampling valve 32 is then pivoted so that pointer 106a of handle 106 of sampling valve 32 is pointing towards the word "SAMPLE" inscribed on legend plate 104. This in turn rotates pivotable valve member 88 within insert member 60 of sampling valve 32 from its position wherein diagonal bore 100 of pivotable valve member 88 is in fluid-flow connection with (a) the third or lower central port 78 of sampling valve 32 and (b) the second or upper horizontally-offset port 76, and to the position in which second circumferential groove 98 of pivotable valve member 88 is in fluid-flow connection with (a) the second or upper horizontally-offset port 76 (leading from standpipe 118) and (b) the fourth or side port leading to sample bottle 122, so that the sample of fluid 12 in standpipe 118 is allowed to drain by gravity into sample bottle 122.

Although fluid-sampling apparatus 10, when in the sample mode, is designed to move fluid from standpipe 118 to sample bottle 122 by gravity flow, a vacuum may be applied via vacuum connection 146 and tubing 148 or pressurizing overflow chamber 120 via three-way valve 126 may also be used to help sample of fluid 12 from standpipe 118 to flow to sample bottle 122, if necessary due to the high viscosity of fluid 12 or otherwise. This provides an alternative to gravity flow.

It should be noted that the volumetric capacity of standpipe 118 is only about 80 percent of the volumetric capacity of sample bottle 122. This ensures that sample bottle 122 cannot become overfilled by fluid 12 drained from standpipe 118.

Next, handle 106 of sampling valve 28 is pivoted so that pointer 106a points toward the word "DRAIN" inscribed on legend plate 104, and handle 56 of ball valve 34 is pivoted so that ball valve 34 is opened. Pivotable valve member 88 is oriented such that its first circumferential groove 96 is in fluid-flow alignment with the first (or upper central) and third (or lower central) ports 74 and 78 in insert member 60, so that the fluid overflowed from standpipe 118 into overflow chamber 120 can be drained by gravity back into reactor vessel 14.

Although the fluid-sampling apparatus 10 of the present invention, when in the drain mode, is designed to drain by gravity, three-way valve 126 may also be used to pressurize overflow chamber 120 to help push overflowed fluid 12 in overflow chamber 120 back into reactor vessel 14. This provides an alternative means of draining.

Design and operation of fluid-sampling apparatus 10 is such that only corrosion-resistant materials (e.g., borosilicate glass, virgin Teflon, and Hastelloy®) come into contact with the reaction fluid. This is desirable because fluid 12 in reactor vessel 14 may be corrosive.

The form of the present invention shown and described in the disclosure merely represents illustrative embodiments thereof It is to be understood that various changes may be made without departing from the spirit and scope of the invention as defined by the following claims.

We claim:

1. A fluid-sampling apparatus for sampling fluid from a fluid source, comprising:

an overflow chamber assembly defining an overflow chamber therein;

a valve assembly interconnecting the overflow chamber assembly and the fluid source, the valve assembly including a valve movable between a first position wherein the overflow chamber communicates with the fluid source and a second position;

a sample bottle having an interior and being operatively connected to the valve assembly wherein the interior of the sample bottle communicates with the overflow chamber with the valve in the second position, and a vacuum assembly operatively connected to the overflow chamber assembly, the vacuum assembly movable between a first setting wherein the vacuum assembly generates a vacuum to draw fluid into the overflow chamber from the fluid source and a second setting for purging fluid from the overflow chamber.

2. A fluid-sampling apparatus for sampling fluid from a reactor vessel through a sampling port in the reactor vessel, the fluid-sampling apparatus comprising:

a valve assembly including a pivotable valve member defining a middle portion of a fluid inflow passageway and middle portions of first and second fluid outflow passageways, wherein the fluid inflow passageway and the first fluid outflow passageway are in fluid flow alignment with the sampling port of the reactor vessel when the pivotable valve member is pivoted to first and second predetermined positions, respectively;

an inner vessel having an open top, the inner vessel being offset from the longitudinal axis of a lower portion of the fluid inflow passageway; and an outer vessel housing the inner vessel therewithin, wherein the outer vessel is for containing fluid drawn from the reactor vessel into the inner vessel and overflowed from the open top of the inner vessel so that the inner vessel contains an non-contaminated sample of the fluid from the reactor vessel.

3. The fluid-sampling apparatus of claim 2 wherein the pivotable valve member has first and second circumferential grooves therein and a diagonal bore therethrough such that the first and second circumferential grooves and the diagonal bore for the middle portions of the first and second fluid outflow passageways and the fluid inflow passageway, respectively.

4. The fluid-sampling apparatus of claim 3 wherein:

when the pivotable valve member is in the first predetermined position, the diagonal bore is aligned to form part of the fluid inflow passageway, thereby allowing flow of fluid from the reactor vessel through the inner vessel to the outer vessel;

when the pivotable valve member is in the second predetermined position, the second circumferential groove is aligned to form the middle portion of the first fluid flow outflow passageway, thereby allowing flow of fluid from the inner vessel to the sample bottle; and when the pivotable valve member is in the third predetermined position, the first circumferential groove is aligned to form the middle portion of the second outflow passageway, thereby allowing flow of fluid from the outer vessel to the reactor vessel.

5. The fluid-sampling apparatus of claim 4 comprising a shell and an insert member therein, the pivotable valve member being within the insert member, complementarily shaped therewith and pivotable therewithin.

6. The fluid-sampling apparatus of claim 5 wherein:

the first circumferential groove spans approximately one-hundred-eighty degrees about the pivotable valve member; and the second circumferential groove spans approximately ninety degrees about the pivotable valve member.

7. The fluid-sampling apparatus of claim 2 wherein the inner vessel is a standpipe having an open top and open bottom, the open bottom being connected in fluid-flow relation to the valve assembly, the standpipe having a tapered inside bottom surface for preventing a fluid from remaining within the standpipe.

8. The fluid-sampling apparatus of claim 2 wherein the outer vessel has a volume capacity fifteen to twenty times the volume capacity of the inner vessel, thereby to assure capacity for fluid overflowing from the standpipe.

9. The fluid-sampling apparatus of claim 2 further comprising a ball check valve for preventing contamination of the vacuum assembly.

10. A method of sampling fluid from a reactor vessel comprising:

attaching a fluid-sampling apparatus to the reactor vessel;

vacuum drawing the fluid from the reactor vessel through a valve assembly of the fluid-sampling apparatus and into an inner vessel in an overflow chamber assembly;

overflowing the fluid from the inner vessel into an outer vessel of the overflow chamber assembly; and discontinuing the vacuum drawing.

11. The method of sampling fluid of claim 10 wherein, after discontinuing the vacuum drawing, pivoting a pivotable valve member to a sample position so that fluid in the inner vessel drains by gravity into a sample bottle.

12. The method of sampling fluid of claim 11 wherein, after fluid drains to the sample bottle, pivoting the pivotable valve member to a drain position so that fluid which has overflowed into the outer vessel drains by gravity into the reactor vessel.

13. A fluid-sampling apparatus comprising:

a valve assembly having a sampling valve including an outer shell, an insert member, and a pivotable valve member such that the outer shell houses the insert member therewithin and the insert member has a central space therewithin for housing the pivotable valve member;

an overflow chamber assembly connected to the valve assembly;

a vacuum assembly connected to the overflow chamber assembly;

a sample bottle mounting assembly connected to both the valve assembly and the vacuum assembly;

a legend plate inscribed with three predetermined positions, and a handle connected to the pivotable valve member with a pointer for pointing at one of the three predetermined positions on a legend plate.

14. A fluid-sampling apparatus comprising:

a valve assembly having a sampling valve including an outer shell, an insert member, and a pivotable valve member such that the outer shell houses the insert member therewithin and the insert member has a central space therewithin for housing the pivotable valve member;

and wherein the pivotable valve member has a main body portion with first and second circumferential grooves therein and a diagonal bore therethrough and a second portion for connection to a handle for pivoting the pivotable valve member;

an overflow chamber assembly connected to the valve assembly;

a vacuum assembly connected to the overflow chamber assembly; and a sample bottle mounting assembly connected to both the valve assembly and the vacuum assembly.

15. The fluid-sampling apparatus of claim 14 wherein the insert member has first, second, third and fourth ports leading from various positions on an outer periphery thereof to the central space therewithin such that, when the pivotable valve member is pivoted to first, second and third predetermined positions, the first and second circumferential grooves and the diagonal bore are aligned with various combinations of the first, second, third and fourth ports in the insert member.

16. The fluid-sampling apparatus of claim 15 wherein the outer shell has an open top and the insert member has an upwardly-extending portion extending through the open top, the upwardly-extending portion having a tapered top drain surface converging downwardly to the first port to facilitate drainage, the top drain surface having the second port laterally offset from the first port.

17. The fluid-sampling apparatus of claim 16 wherein the insert member has a tubular extending lower portion having the third port therethrough.

18. A fluid-sampling apparatus comprising:
a valve assembly;
an overflow chamber assembly connected to the valve assembly, the overflow assembly including an inner vessel housed within an outer vessel, the outer vessel forming an overflow chamber for containing fluid overflowed from a top of the inner vessel, and at least a portion of the outer vessel being transparent for viewing inside the overflow chamber;
a vacuum assembly connected to the overflow chamber assembly; and
a sample bottle mounting assembly connected to both the valve assembly and the vacuum assembly.

19. The fluid-sampling apparatus of claim 18, wherein the inner vessel is a standpipe having an open top and open bottom, the open bottom being connected in fluid-flow relation to the valve assembly.

20. The fluid-sampling apparatus of claim 19 wherein:
the valve assembly includes a sampling valve comprising an outer shell, an insert member, and a pivotable valve member such that the outer shell houses the insert member therewithin and the insert member has a central space therewithin for housing the pivotable valve member;
the insert member has first, second, third and fourth ports leading from various positions on an outer periphery thereof to the central space therewithin, such that when the pivotable valve member is pivoted to first, second and third predetermined positions, first and second circumferential grooves in the pivotable valve member and a diagonal bore therethrough are aligned with various combinations of the first, second, third, and fourth ports in the insert member; and
the outer shell has an open top and the insert member has an upwardly-extending portion extending through the open top, the upwardly-extending portion having a tapered top drain surface, the top drain surface (a) downwardly converging to the first port to facilitate drainage and (b) having the second port laterally offset from the first port and engaged with the open bottom of the standpipe.

* * * * *